United States Patent
Metten et al.

(10) Patent No.: US 9,173,831 B2
(45) Date of Patent: *Nov. 3, 2015

(54) PRODUCT FOR KERATIN CONTAINING FIBERS, CONTAINING AT LEAST ONE SPECIFIC AMPHIPHILIC CATONIC POLYMER AND AT LEAST A POLYMER WITH STRUCTURAL UNITS DERIVED FROM MALEIC ACID

(71) Applicant: Henkel AG & Co. KGaA, Dusseldorf (DE)

(72) Inventors: Diane Metten, Hamburg (DE); Bernd Richters, Hamburg (DE); Rene Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,891

(22) PCT Filed: Nov. 20, 2012

(86) PCT No.: PCT/EP2012/073098
§ 371 (c)(1),
(2) Date: Jun. 19, 2014

(87) PCT Pub. No.: WO2013/092075
PCT Pub. Date: Jun. 27, 2013

(65) Prior Publication Data
US 2015/0004125 A1    Jan. 1, 2015

(30) Foreign Application Priority Data
Dec. 22, 2011    (DE) .......... 10 2011 089 564

(51) Int. Cl.
| | |
|---|---|
| A61Q 5/04 | (2006.01) |
| A61K 8/88 | (2006.01) |
| A61Q 5/06 | (2006.01) |
| A61K 8/81 | (2006.01) |
| A45D 7/04 | (2006.01) |

(52) U.S. Cl.
CPC ... *A61K 8/88* (2013.01); *A45D 7/04* (2013.01); *A61K 8/8129* (2013.01); *A61K 8/8164* (2013.01); *A61K 8/8182* (2013.01); *A61Q 5/06* (2013.01); *A61K 2800/20* (2013.01); *A61K 2800/594* (2013.01)

(58) Field of Classification Search
CPC ..... A61Q 5/06; A61K 8/8182; A61K 8/8129; A61K 8/88; A61K 2800/594
USPC .......................... 424/70.16, 70.17
See application file for complete search history.

(56) References Cited

U.S. PATENT DOCUMENTS 4,240,450 A * 12/1980 Grollier et al. ............. 132/209

FOREIGN PATENT DOCUMENTS

| DE | 19756454 C1 | 6/1999 | |
|---|---|---|---|
| DE | 102008038105 A1 | 2/2010 | |
| EP | 998908 A2 | 5/2000 | |
| WO | 9222701 A1 | 12/1992 | |
| WO | WO 2010/020500 A2 * | 2/2010 | ............ A61Q 5/06 |

OTHER PUBLICATIONS

STIC Search Report dated Oct. 20, 2014.*
English traslation of the Patent WO 2010/020500 A2 dated Dec. 4, 2014.*
International Search Report completed Nov. 25, 2013 in PCT/EP2012/073098.

* cited by examiner

*Primary Examiner* — Eisa Elhilo
(74) *Attorney, Agent, or Firm* — P. Scott Smith

(57) ABSTRACT

Agents for treating keratin-containing fibers, in particular human hair, are provided. The agents comprise, in a cosmetically acceptable carrier, (a) at least one amphiphilic cationic polymer comprising respectively at least one structural unit of the formulae (I) to (IV), as provided herein, and (b) at least one copolymer comprising at least one structural unit of formula (A1) and at least one structural unit of formula (A2), as provided herein, the use of said agent for temporarily styling hair and for hair care, in particular as an aerosol hairspray or an aerosol hair mousse.

19 Claims, No Drawings

US 9,173,831 B2

PRODUCT FOR KERATIN CONTAINING FIBERS, CONTAINING AT LEAST ONE SPECIFIC AMPHIPHILIC CATONIC POLYMER AND AT LEAST A POLYMER WITH STRUCTURAL UNITS DERIVED FROM MALEIC ACID

CROSS REFERENCE TO RELATED APPLICATIONS

The present disclosure is a U.S. National Stage entry under 35 U.S.C. §371 based on International Application No. PCT/EP2012/073098, filed Nov. 20, 2012 which was published under PCT Article 21(2) and which claims priority to German Patent Application No. DE 10 2011 089 564.7 filed on Dec. 22, 2011, which is incorporated herein by reference in its entirety.

TECHNICAL FIELD

The technical field relates to agents for hair treatment containing a combination of at least one amphiphilic cationic polymer with at least one polymer having structural units derived from maleic acid ester, to the use of said agents for the temporary deformation and/or care of keratin-containing fibers, and to aerosol hair sprays/foams based on said agents.

BACKGROUND

"Keratinic fibers" are understood in principle as all animal hairs, e.g. wool, horsehair, angora hair, furs, feathers, and products or textiles produced therefrom. Preferably, however, the keratinic fibers are human hairs.

An attractive-looking hairstyle is generally regarded these days as an indispensable element of a well-groomed appearance. Given the currents of fashion, more and more hairstyles regarded as chic are ones that, for many types of hair, can be constructed, or maintained for a longer period of time of up to several days, only with the use of setting active agents. Hair treatment agents that serve for permanent or temporary shaping of the hair therefore play an important role. Temporary shaping results that are intended to result in good hold without impairing the healthy appearance of the hair, for example its shine, can be achieved e.g. using hair sprays, hair waxes, hair gels, hair foams, blow-dry waves, etc.

Corresponding agents for temporary shaping usually contain synthetic polymers as a shaping component. Preparations that contain a dissolved or dispersed polymer can be applied onto the hair by means of propellant gases or using a pump mechanism. Hair gels and hair waxes in particular, however, are as a rule not applied directly onto the hair but instead are distributed in the hair using a comb or the hands.

The most important property of an agent for the temporary deformation of keratinic fibers, hereinafter also called a "styling agent," is to impart the strongest possible hold to the treated fibers in the shape that is generated. If the keratinic fibers involved are human hairs, terms also used are a strong "hairstyle hold" or a high "degree of hold" of the styling agent. The hairstyle hold is determined substantially by the nature and quantity of the setting polymer used, although the further constituents of the styling agent can also have an influence.

In addition to a high degree of hold, styling agents must meet a large number of further requirements. These can be subdivided roughly into: properties on the hair; properties of the particular formulation, e.g. properties of the foam, gel, or sprayed aerosol; and properties that relate to the handling of the styling agent, the properties on the hair being of particular importance. Moisture resistance, low tack, and a balanced conditioning effect may be mentioned in particular. In addition, a styling agent should be universally usable for, if possible, all types of hair.

A plurality of synthetic polymers that are utilized in styling agents have already been developed in order to meet the various requirements. The polymers can be subdivided into cationic, anionic, nonionic, and amphoteric film-forming and/or setting polymers. Ideally, upon application onto the hair in even a small quantity, the polymers yield a polymer film that on the one hand imparts a strong hold to the hairstyle but on the other hand is sufficiently flexible not to break under stress. If the polymer film is too brittle, this results in the formation of so-called "film plaques," i.e. residues that detach as the hair moves and give the impression that the user of the corresponding styling agent has dandruff.

It is still difficult to develop styling agents that exhibit all desired properties in combination. This is true in particular for the combination of strong hold on the one hand, and simple, uniform application onto the keratin-containing fibers on the other hand.

SUMMARY

An object herein is therefore to furnish an agent for the temporary deformation and/or care of keratinic fibers that is notable for a high degree of hold and for a good care-providing effect, and in particular possesses outstanding ease of handling during application onto the keratinic fibers.

DETAILED DESCRIPTION

It has now been found, surprisingly, that agents for the temporary deformation and/or care of keratinic fibers that are notable for a high degree of hold and for a good care-providing effect can be achieved by way of a combination of certain polymers. It has furthermore been possible in the context of some embodiments to provide, in addition to these outstanding properties, compositions having no turbidity. Freedom from turbidity matters in particular in the context of the provision of aerosol compositions, since solid suspended particles can result in clogging of the exit nozzle of the aerosol package. In the case of turbid and low-viscosity compositions a general risk of sedimentation additionally exists, which has a disadvantageous effect on the shelf stability of the composition.

A first embodiment is a cosmetic agent for cosmetic treatment of keratin-containing fibers, in particular human hair, containing in a cosmetically acceptable carrier (a) at least one amphiphilic cationic polymer comprising at least one structural unit of formula (I), at least one structural unit of formula (II), at least one structural unit of formula (III), and at least one structural unit of formula (IV),

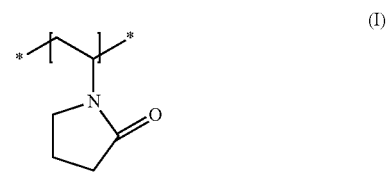

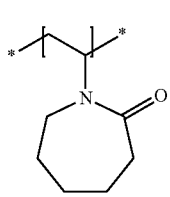
(II)

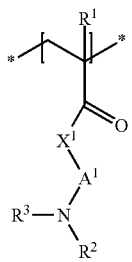
(III)

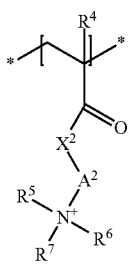
(IV)

in which
R¹ and R⁴ mutually independently denote a hydrogen atom or a methyl group,
X¹ and X² mutually independently denote an oxygen atom or an NH group,
A¹ and A² mutually independently denote an ethane-1,2-diyl group, propane-1,3-diyl group, or butane-1,4-diyl group,
R², R³, R⁵, and R⁶ mutually independently denote a ($C_1$ to $C_4$) alkyl group,
R⁷ denotes a ($C_8$ to $C_{30}$) alkyl group, and
(b) at least one copolymer comprising at least one structural unit of formula (A1) and at least one structural unit of formula (A2),

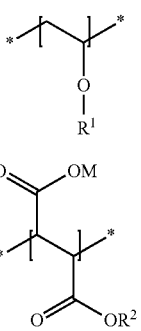
(A1)

(A2)

in which
R¹ denotes a ($C_1$ to $C_{18}$) alkyl group,
R² denotes a ($C_1$ to $C_6$) alkyl group,
M denotes a hydrogen atom or an equivalent of a mono- or polyvalent cation.

In the formulas above and all formulas to follow, a chemical bond identified by the symbol * denotes a free valence of the corresponding structural fragment.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge.

Examples of ($C_1$ to $C_4$) alkyl groups are methyl, ethyl, propyl, isopropyl, butyl, sec-butyl, isobutyl, tert-butyl.

Examples of ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

Examples of ($C_4$ to $C_{12}$) alkylaminocarbonyl groups are butylaminocarbonyl, sec-butylaminocarbonyl, isobutylaminocarbonyl, tert-butylaminocarbonyl, (2,4,4-trimethylpent-2-yl)aminocarbonyl, neopentylaminocarbonyl, 2-ethylhexylaminocarbonyl, neodecylaminocarbonyl.

Examples of ($C_4$ to $C_{12}$) alkylaminoethylaminocarbonyl groups are butylaminoethylaminocarbonyl, sec-butylaminoethylaminocarbonyl, isobutylaminoethylaminocarbonyl, tert-butylaminoethylaminocarbonyl, (2,4,4-trimethylpent-2-yl)aminoethylaminocarbonyl, neopentyl-aminoethylaminocarbonyl, 2-ethylhexylaminoethylaminocarbonyl, neodecylaminoethylaminocarbonyl.

Examples of ($C_4$ to $C_{12}$) alkylaminopropylaminocarbonyl groups are butylaminopropylaminocarbonyl, sec-butylaminopropylaminocarbonyl, isobutylaminopropylaminocarbonyl, tert-butylaminopropylaminocarbonyl, (2,4,4-trimethylpent-2-yl)aminopropylaminocarbonyl, neopentylaminopropylaminocarbonyl, 2-ethylhexylaminopropylaminocarbonyl, neodecylaminopropylaminocarbonyl.

Examples of ($C_4$ to $C_{12}$) alkyloxycarbonyl groups are butyloxycarbonyl, sec-butyloxycarbonyl, isobutyloxycarbonyl, tert-butyloxycarbonyl, (2,4,4-trimethylpent-2-yl)oxycarbonyl, neopentyloxycarbonyl, 2-ethylhexyloxycarbonyl, neodecyloxycarbonyl.

Examples of ($C_4$ to $C_{12}$) alkylaminoethyloxycarbonyl groups are butylaminoethyloxycarbonyl, sec-butylaminoethyloxycarbonyl, isobutylaminoethyloxycarbonyl, tert-butylaminoethyl-oxycarbonyl, (2,4,4-trimethylpent-2-yl)aminoethyloxycarbonyl, neopentylaminoethyloxycarbonyl, 2-ethylhexylaminoethyloxycarbonyl, neodecylaminoethyloxycarbonyl.

Examples of ($C_4$ to $C_{12}$) alkylaminopropyloxycarbonyl groups are butylaminopropyloxycarbonyl, sec-butylaminopropyloxycarbonyl, isobutylaminopropyloxycarbonyl, tert-butylaminopropyloxycarbonyl, (2,4,4-trimethylpent-2-yl) aminopropyloxycarbonyl, neopentylaminopropyloxycarbonyl, 2-ethylhexylaminopropyloxycarbonyl, neodecylaminopropyloxycarbonyl.

Examples of ($C_4$ to $C_{12}$) alkyl groups are butyl, sec-butyl, isobutyl, tert-butyl, 2,4,4-trimethylpent-2-yl, neopentyl, 2-ethylhexyl, neodecyl.

Examples of ($C_2$ to $C_{12}$) acyloxy groups are acetoxy, propionyloxy, and neodecanoyloxy.

In some embodiments, agents contain the amphiphilic cationic polymers (a) in a quantity from about 0.05 wt % to about 8.0 wt %, particularly preferably from about 0.1 wt % to about 5.0 wt %, very particularly preferably from about 0.2 to about 2.5 wt %, based in each case on the total weight of the agent.

Preferred agents contain the copolymers (b) in a quantity from about 0.05 wt % to about 8.0 wt %, particularly preferably from about 0.1 wt % to about 5.0 wt %, very particularly preferably from about 0.2 to about 2.5 wt %, based in each case on the total weight of the agent.

In some embodiments, a cosmetic agent contains the amphiphilic cationic polymers of component (a) and the copolymers of component (b) in a weight ratio range of (a) to (b) from about 5 to 1 to about 1 to 5, in particular from about 2 to 1 to about 1 to 2.

In some embodiments, the amphiphilic cationic polymers have a molecular weight from about 10,000 g/mol to about 50,000,000 g/mol, in particular from about 50,000 g/mol to about 5,000,000 g/mol, particularly preferably from about 75,000 g/mol to about 1,000,000 g/mol.

The properties of the agent prove to be particularly advantageous when formulated as an aerosol spray, aerosol foam, pump spray, or pump foam. This preferred formulation form is described later in detail.

In some embodiments, the amphiphilic cationic polymers (a) conform, in terms of the aforementioned formulas (I) to (IV), to one or more of the following features:
- $R^1$ and $R^4$ each signify a methyl group,
- $X^1$ denotes an NH group,
- $X^2$ denotes an NH group,
- $A^1$ and $A^2$ mutually independently denote ethane-1,2-diyl or propane-1,3-diyl,
- $R^2$, $R^3$, $R^5$, and $R^6$ mutually independently denote methyl or ethyl (particularly preferably methyl),
- $R^7$ denotes a ($C_{10}$ to $C_{24}$) alkyl group, in particular in particular decyl (caprinyl), dodecyl (lauryl), tetradecyl (myristyl), hexadecyl (cetyl), octadecyl (stearyl), eicosyl (arachyl), or docosyl (behenyl).

In some embodiments, the structural unit of formula (III) is selected from at least one structural unit of formulas (III-1) to (III-8).

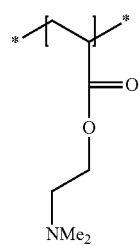

(III-1)

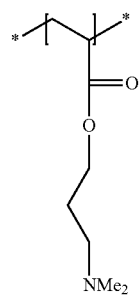

(III-2)

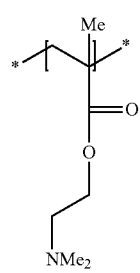

(III-3)

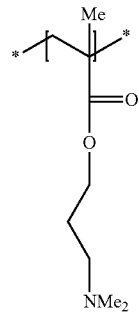

(III-4)

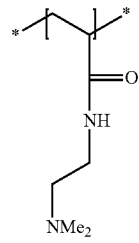

(III-5)

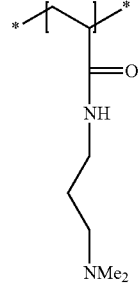

(III-6)

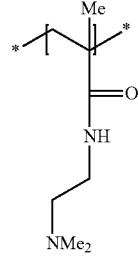

(III-7)

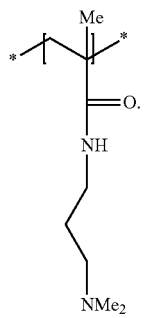

(III-8)

In some embodiments, a structural unit of formula (III) is selected from the structural unit in accordance with formula (III-7) and/or formula (III-8). The structural unit of formula (III-8) is a very particularly preferred structural unit.

In some embodiments, the structural unit of formula (IV) is selected from at least one structural unit of formulas (IV-1) to (IV-8)

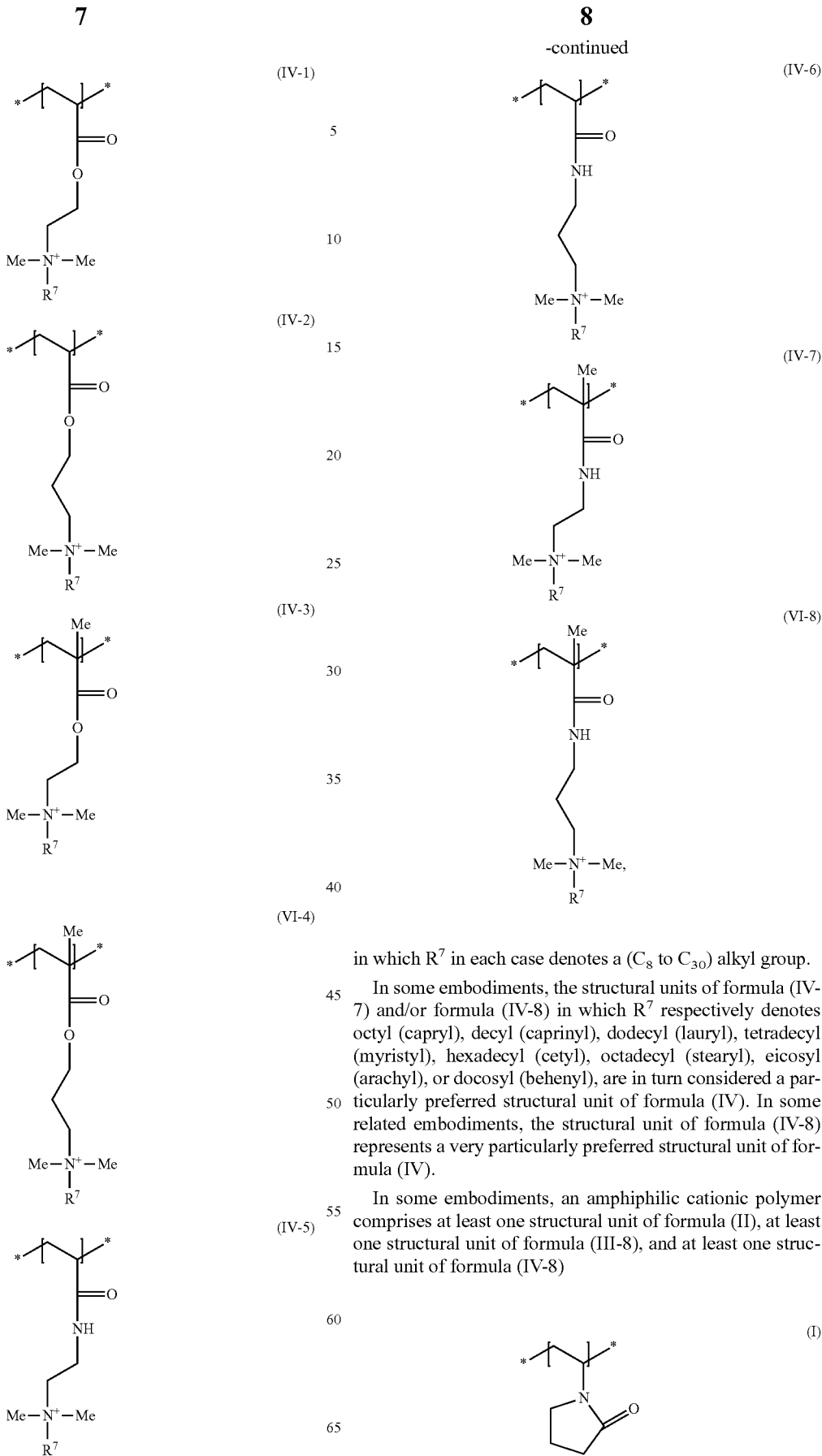

in which $R^7$ in each case denotes a ($C_8$ to $C_{30}$) alkyl group.

In some embodiments, the structural units of formula (IV-7) and/or formula (IV-8) in which $R^7$ respectively denotes octyl (capryl), decyl (caprinyl), dodecyl (lauryl), tetradecyl (myristyl), hexadecyl (cetyl), octadecyl (stearyl), eicosyl (arachyl), or docosyl (behenyl), are in turn considered a particularly preferred structural unit of formula (IV). In some related embodiments, the structural unit of formula (IV-8) represents a very particularly preferred structural unit of formula (IV).

In some embodiments, an amphiphilic cationic polymer comprises at least one structural unit of formula (II), at least one structural unit of formula (III-8), and at least one structural unit of formula (IV-8)

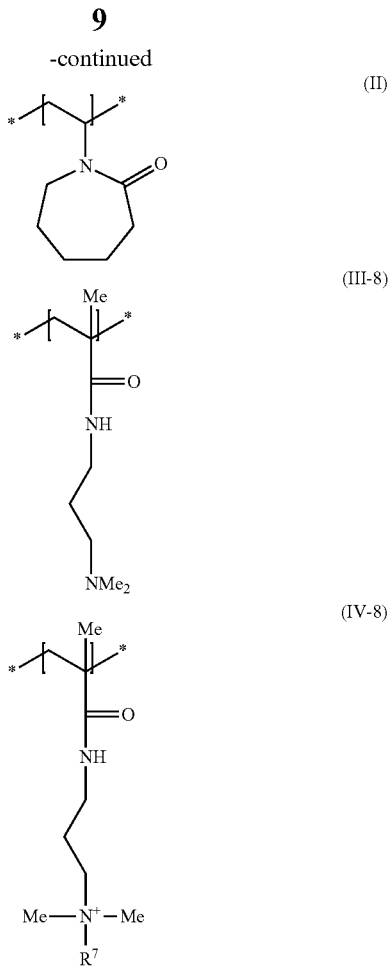

in which $R^2$ denotes octyl (capryl), decyl (caprinyl), dodecyl (lauryl), tetradecyl (myristyl), hexadecyl (cetyl), octadecyl (stearyl), eicosyl (arachyl), or docosyl (behenyl).

In some embodiments, a very particularly preferred amphiphilic cationic polymer is the copolymer of N-vinylpyrrolidone, N-vinylcaprolactam, N-(3-dimethylaminopropyl)methacrylamide, and 3-(methacryloylamino)propyl-lauryldimethylammonium chloride (INCI name: Polyquaternium-69) that is marketed, for example, by the ISP company under the commercial name AquaStyle® 300 (30 wt % active substance in ethanol/water mixture, molecular weight 350,000).

In addition to the aforesaid amphiphilic cationic polymer of component (a), the agent contains as component (b) at least one previously defined polymer having structural units derived from maleic acid ester (see above). This aforesaid polymer is, self-evidently, different from the compounds of component (a).

In some embodiments, $R^1$ in accordance with formula (A1) denotes a methyl group.

In some embodiments, $R^2$ in accordance with formula (A2) denotes a ($C_2$ to $C_4$) alkyl group, in particular ethyl, n-propyl, isopropyl, n-butyl, or tert-butyl.

If the structural units of formula (A2) are present with a carboxylic acid function, the residue M denotes a hydrogen atom. If the structural units of formula (A2) are present as a salt of the carboxylic acid, M denotes an equivalent of a monovalent or polyvalent cation. The monovalent or polyvalent cation $M^{z+}$ respectively having a valency z of one or higher serves, merely for reasons of electroneutrality, to compensate for the single negative charge of the carboxylate fragment —$COO^{(-)}$ of formula (A2) that is present in the context of salt formation. The equivalent of the corresponding cation that is to be used is equal to $1/z$. In the case of salt formation, the fragment —COOM of formula (I) denotes the group:

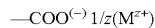

All physiologically acceptable cations are suitable in principle as monovalent or polyvalent cations $M^{z+}$. These are, in particular, metal cations of the physiologically acceptable metals from groups Ia, Ib, IIa, IIb, IIIb, VIa, or VIII of the periodic table of the elements, ammonium ions, as well as cationic organic compounds having a quaternized nitrogen atom. The latter are formed, for example, by protonation of primary, secondary, or tertiary organic amines (in particular ($C_2$ to $C_6$) alkanolamines (see below: neutralization of the aforesaid polymers with ($C_2$ to $C_6$ alkanolamines)) with an acid, for example with structural units of formula (A2) in their acid form, or by permanent quaternization of the said organic amines. Examples of these cationic organic ammonium compounds are 2-ammonioethanol and 2-trimethylammonioethanol. M in formula (A2) preferably denotes a hydrogen atom, an ammonium ion, an alkali metal ion, or a hydroxy-($C_2$ to $C_6$) alkylammonium ion, particularly preferably a hydrogen atom, an ammonium ion, hydroxy-($C_2$ to $C_6$) alkylammonium ion, a sodium ion, or a potassium ion.

In some embodiments, tt is preferred if the agents contain as component (b) at least one polymer selected from at least one polymer of the group having polymers of INCI nomenclature Butyl Ester of PVM/MA Copolymer, Isopropyl Ester of PVM/MA Copolymer, Ethyl Ester of PVM/MA Copolymer.

Corresponding polymers of component (b) of the agent are commercialized, for example, under the commercial name Gantrez® ES 425 (copolymer of methyl vinyl ether and the butyl semi-ester of maleic acid; 50 wt % active substance in ethanol; INCI name: Butyl Ester of PVM/MA Copolymer (Ashland)), Gantrez® ES 435 (copolymer of methyl vinyl ether and the butyl semi-ester of maleic acid; 50 wt % active substance in isopropanol; INCI name: Butyl Ester of PVM/MA Copolymer (Ashland)), Gantrez® ES 335I (copolymer of methyl vinyl ether and the isopropyl semi-ester of maleic acid; 50 wt % active substance in isopropanol; INCI name: Butyl Ester of PVM/MA Copolymer (Ashland)), Gantrez® ES 225 (copolymer of methyl vinyl ether and the ethyl semi-ester of maleic acid; 50 wt % active substance in ethanol; INCI name: Ethyl Ester of PVM/MA Copolymer (Ashland)).

The following are exemplary embodiments of cosmetic agents:

(A) An agent for cosmetic treatment of keratin-containing fibers, in particular human hair, containing in a cosmetically acceptable carrier (a) at least one amphiphilic cationic polymer comprising at least one structural unit of formula (I), at least one structural unit of formula (II), at least one structural unit of formula (III-8), and at least one structural unit of formula (IV-8),

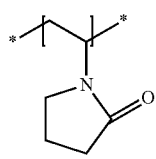 (I)

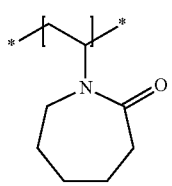 (II)

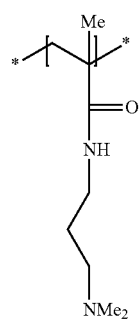 (III-8)

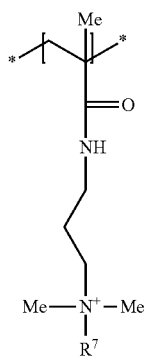 (IV-8)

in which R⁷ denotes octyl (capryl), decyl (caprinyl), dodecyl (lauryl), tetradecyl
(myristyl), hexadecyl (cetyl), octadecyl (stearyl), eicosyl (arachyl), or docosyl (behenyl)

and (b) at least one copolymer comprising at least one structural unit of formula (A1) and at least one structural unit of formula (A2),

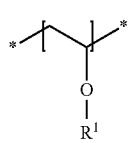 (A1)

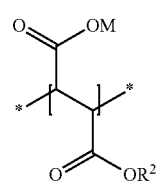 (A2)

in which

R¹ denotes a methyl group,

R² denotes an ethyl group, an n-propyl group, an isopropyl group, an n-butyl group, or a tert-butyl group, M denotes a hydrogen atom or an equivalent of a mono- or polyvalent cation.

(B) An agent for cosmetic treatment of keratin-containing fibers, in particular human hair, containing in a cosmetically acceptable carrier (a) at least one amphiphilic cationic polymer having the INCI nomenclature Polyquaternium-69, and (b) at least one copolymer selected from at least one polymer of the group having polymers of INCI nomenclature Butyl Ester of PVM/MA Copolymer, Isopropyl Ester of PVM/MA Copolymer, Ethyl Ester of PVM/MA Copolymer.

(C) An agent for cosmetic treatment of keratin-containing fibers, in particular human hair, containing in a cosmetically acceptable carrier (a) about 0.05 wt % to about 8.0 wt %, preferably from about 0.1 wt % to about 5.0 wt %, particularly preferably from about 0.2 to about 2.5 wt % of at least one amphiphilic cationic polymer comprising at least one structural unit of formula (I), at least one structural unit of formula (II), at least one structural unit of formula (III-8), and at least one structural unit of formula (IV-8),

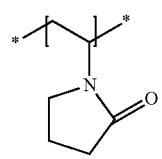 (I)

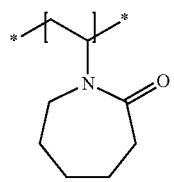 (II)

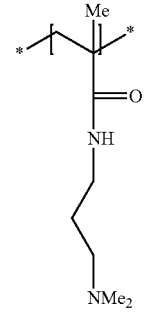 (III-8)

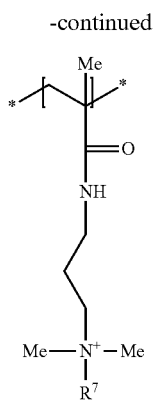

(IV-8)

in which R⁷ denotes octyl (capryl), decyl (caprinyl), dodecyl (lauryl), tetradecyl
(myristyl), hexadecyl (cetyl), octadecyl (stearyl), eicosyl (arachyl), or docosyl (behenyl)
and
(b) about 0.05 wt % to about 8.0 wt %, preferably from about 0.1 wt % to about 5.0 wt %, particularly preferably from about 0.2 to about 2.5 wt % of at least one copolymer comprising at least one structural unit of formula (A1) and at least one structural unit of formula (A2),

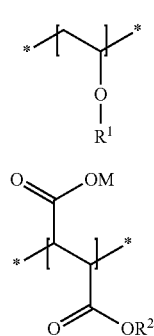

in which
R¹ denotes a methyl group,
R² denotes an ethyl group, an n-propyl group, an isopropyl group, an n-butyl group, or a tert-butyl group,
M denotes a hydrogen atom or an equivalent of a mono- or polyvalent cation.

(D) An agent for cosmetic treatment of keratin-containing fibers, in particular human hair, containing in a cosmetically acceptable carrier
(a) about 0.05 wt % to about 8.0 wt %, preferably from about 0.1 wt % to about 5.0 wt %, particularly preferably from about 0.2 to about 2.5 wt % of at least one amphiphilic cationic polymer having the INCI nomenclature Polyquaternium-69,
and
(b) about 0.05 wt % to about 8.0 wt %, preferably from about 0.1 wt % to about 5.0 wt %, particularly preferably from about 0.2 to about 2.5 wt % of at least one copolymer selected from at least one polymer of the group having polymers of INCI nomenclature Butyl Ester of PVM/MA Copolymer, Isopropyl Ester of PVM/MA Copolymer, Ethyl Ester of PVM/MA Copolymer.

In some embodiments, it is particularly preferred if the copolymers of component (b) are present in entirely or partly neutralized fashion in the salt form. At least one (C₂ to C₆) alkanolamine is preferably used for neutralization. For this reason, in some embodiments agents (in particular the preferred embodiments (A) to (D)) additionally contain at least one (C₂ to C₆) alkanolamine. The alkanolamines usable as an alkalizing agent are preferably selected from primary amines having a C₂ to C₆ alkyl basic structure that carries at least one hydroxyl group. Particularly preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. In some particular embodiments, alkanolamines are selected from the group of: 2-aminoethan-1-ol, 2-amino-2-methylpropan-1-ol, and 2-amino-2-methylpropane-1,3-diol.

The agents preferably have at 20° C. a pH value from about pH 4 to about pH 9, particularly preferably from about pH 6 to about pH 7.

In order to intensify the effect, in some embodiments, the agents additionally contain at least one surfactant, wherein nonionic, anionic, cationic, ampholytic surfactants are suitable in principle. The group of ampholytic or amphoteric surfactants encompasses zwitterionic surfactants and ampholytes. In some embodiments, the surfactants can already have an emulsifying effect.

In some embodiments, additional surfactants are contained in the agent preferably in a quantity from about 0.01 wt % to about 5 wt %, particularly preferably from about 0.05 wt % to about 0.5 wt %, based in each case on the weight of the agent.

In some embodiments, it has proven to be particularly preferred if the agents additionally contain at least one nonionic surfactant.

Nonionic surfactants contain as a hydrophilic group, for example, a polyol group, a polyalkylene glycol ether group, or a combination of a polyol group and polyglycol ether group. Such compounds are, for example
- addition products of 2 to 100 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group,
- addition products, end-capped with a methyl residue or C₂ to C₆ alkyl residue, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, for example the grades obtainable under the marketing designations Dehydrol® LS, Dehydrol® LT (Cognis),
- C₁₂ to C₃₀ fatty acid mono- and diesters of addition products of 1 to 30 mol ethylene oxide with glycerol,
- addition products of 5 to 60 mol ethylene oxide with castor oil and hardened castor oil,
- polyol fatty acid esters, for example the commercial product Hydagen® HSP (Cognis), or Sovermol grades (Cognis),
- alkoxylated triglycerides,
- alkoxylated fatty acid alkyl esters of formula (E4-I)

$$R^1CO\text{---}(OCH_2CHR^2)_wOR^3 \quad (E4\text{-}I),$$

in which R¹CO denotes a linear or branched, saturated and/or unsaturated acyl residue having 6 to 22 carbon atoms, R² denotes hydrogen or methyl, R³ denotes linear or branched alkyl residues having 1 to 4 carbon atoms, and w denotes numbers from 1 to 20, amine oxides, hydroxy mixed ethers, for example as described in German Application 19738866, sorbitan fatty acid esters and addition products of ethylene oxide with sorbitan fatty acid esters, for example polysorbates, sugar fatty acid esters and addition products of ethylene oxide with sugar fatty acid esters, addition products of ethylene oxide with fatty acid alkanolamides and fatty amines, sugar surfactants of the alkyl and alkenyl oligoglycoside types, in accordance with formula (E4-II)

$$R^4O\text{-}[G]_p \tag{E4-II}$$

in which $R^4$ denotes an alkyl or alkenyl residue having 4 to 22 carbon atoms, G denotes a sugar residue having 5 or 6 carbon atoms, and p denotes numbers from 1 to 10. They can be obtained using the relevant methods of preparative organic chemistry.

In some embodiments, alkylene oxide addition products with saturated linear fatty alcohols and fatty acids, having respectively about 2 to about 100 mol ethylene oxide per mol of fatty alcohol or fatty acid, have proven to be very particularly preferred nonionic surfactants. Preparations having outstanding properties are likewise obtained when they contain $C_{12}$ to $C_{30}$ fatty acid mono- and diesters of addition products of about 1 to about 30 mol ethylene oxide with glycerol, and/or addition products of about 5 to about 60 mol ethylene oxide with castor oil and hardened castor oil, as nonionic surfactants.

In some embodiments, the agents contain as a surfactant at least one addition product of about 15 to about 100 mol ethylene oxide, in particular of about 15 to about 50 mol ethylene oxide, with a linear or branched (in particular linear) fatty alcohol having 8 to 22 carbon atoms. This refers very particularly preferably to Ceteareth-15, Ceteareth-25, or Ceteareth-50, which are marketed as Eumulgin® CS 15 (COGNIS), Cremophor A25 (BASF SE), or Eumulgin® CS 50 (COGNIS).

All anionic surface-active substances suitable for use on the human body are, in principle, appropriate as anionic surfactants. These are characterized by an anionic group imparting water solubility, for example a carboxylate, sulfate, sulfonate, or phosphate group, and a lipophilic alkyl group having approximately 8 to 30 carbon atoms. Glycol ether or polyglycol ether groups, ester, ether, and amide groups, and hydroxyl groups can additionally be contained in the molecule. Examples of suitable anionic surfactants are, in each case in the form of the sodium, potassium, and ammonium salts and the mono-, di, and trialkanolammonium salts having 2 to 4 carbon atoms in the alkanol group:

linear and branched fatty acids having 8 to 30 carbon atoms (soaps), ether carboxylic acids of the formula R—O—(CH$_2$—CH$_2$O)$_x$—CH$_2$—COOH, in which R is a linear alkyl group having 8 to 30 carbon atoms and x=0 or is 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic acid mono- and dialkyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups, linear alkanesulfonates having 8 to 24 carbon atoms, linear alpha-olefinsulfonates having 8 to 24 carbon atoms, alpha-sulfo fatty acid methyl esters of fatty acids having 8 to 30 carbon atoms, alkyl sulfates and alkyl polyglycol ether sulfates of the formula R—O(CH$_2$—CH$_2$—O)$_x$—OSO$_3$H, in which R is a preferably linear alkyl group having 8 to 30 carbon atoms and x=0 or is 1 to 12, mixtures of surface-active hydroxysulfonates, sulfated hydroxyalkylpolyethylene glycol ethers and/or hydroxyalkylenepropylene glycol ethers, sulfonates of unsaturated fatty acids having 8 to 24 carbon atoms and 1 to 6 double bonds, esters of tartaric acid and citric acid with alcohols representing addition products of approximately 2 to 15 molecules of ethylene oxide and/or propylene oxide with fatty alcohols having 8 to 22 carbon atoms, sulfated fatty acid alkylene glycol esters of formula (E1-II)

$$R^7CO(AlkO)_nSO_3M \tag{E1-II}$$

in which $R^7CO$ denotes a linear or branched, aliphatic, saturated and/or unsaturated acyl residue having 6 to 22 carbon atoms, Alk denotes CH$_2$CH$_2$, CHCH$_3$CH$_2$, and/or CH$_2$CHCH$_3$, n denotes numbers from 0.5 to 5, and M denotes a cation, as described in German Application 197 36 906, amide ether carboxylic acids, condensation products of $C_8$ to $C_{30}$ fatty alcohols with protein hydrolysates and/or amino acids and derivatives thereof, known to one skilled in the art as protein fatty acid condensates, such as, for example, the Lamepon® grades, Gluadin® grades, Hostapon® KCG, or the Amisoft® grades.

In some embodiments, preferred anionic surfactants are alkyl sulfates, alkyl polyglycol ether sulfates, and ether carboxylic acids having 10 to 18 carbon atoms in the alkyl group and up to 12 glycol ether groups in the molecule, sulfosuccinic acid mono- and dialkyl esters having 8 to 18 carbon atoms in the alkyl group and sulfosuccinic acid monoalkylpolyoxyethyl esters having 8 to 18 carbon atoms in the alkyl group and 1 to 6 oxyethyl groups, monoglycerol disulfites, alkyl and alkenyl ether phosphates, and protein fatty acid condensates.

In some embodiments, cationic surfactants of the quaternary ammonium compound, esterquat, and amidoamine types are also usable. In some embodiments, preferred quaternary ammonium compounds are ammonium halides, in particular chlorides and bromides, such as alkyltrimethylammonium chlorides, dialkyldimethylammonium chlorides, and trialkylmethylammonium chlorides. The long alkyl chains of these surfactants preferably have 10 to 18 carbon atoms, for example as in cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride. Further preferred cationic surfactants are the imidazolium compounds known by the INCI names Quaternium-27 and Quaternium-83.

As used herein, the term "zwitterionic surfactants" refers to those surface-active compounds which carry in the molecule at least one quaternary ammonium group and at least one —COO$^{(-)}$ or SO$_3^{(-)}$ group. In some embodiments, particularly suitable zwitterionic surfactants are the so-called betaines, such as N-alkyl-N,N-dimethylammonium glycinates, for example cocalkyldimethylammonium glycinates, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. In a particular embodiment, a preferred zwitterionic surfactant is the fatty acid amide derivative known by the INCI name Cocamidopropyl Betaine.

As used herein, the term "ampholytes" are understood to be those surface-active compounds which contain in the molecule, besides a $C_8$ to $C_{24}$ alkyl or acyl group, at least one free amino group and at least one —COOH or —SO$_3$H group, and are capable of forming internal salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. In some embodiments, particularly preferred ampholytes are N-cocalkylaminopropionate, cocacylaminoethylaminopropionate, and $C_{12}$ to $C_{18}$ acyl sarcosine.

The agents described herein contain the ingredients or active agents in a cosmetically acceptable carrier.

In some embodiments, preferred cosmetically acceptable carriers are aqueous, alcoholic, or aqueous alcoholic media having preferably at least about 10 wt % water, based on the total agent. The alcohols contained can be, in particular, the lower alcohols having 1 to 4 carbon atoms usually used for cosmetic purposes, for example ethanol and isopropanol.

In some embodiments, it is preferred to use at least one ($C_1$ to $C_4$) monoalkyl alcohol in the agents, in particular in a quantity from about 1 to about 50 wt %, in particular from about 5 to about 30 wt %. This is in turn preferred in particular for packaging as a pump foam or aerosol foam.

Organic solvents or a mixture of solvents having a boiling point below about 400° C. can be contained as additional co-solvents, in a quantity from about 0.1 to about 15 weight percent, preferably from about 1 to about 10 weight percent, based on the total agent. Unbranched or branched hydrocarbons such as pentane, hexane, isopentane, and cyclic hydrocarbons such as cyclopentane and cyclohexane, are particularly suitable as additional co-solvents. Further particularly preferred water-soluble solvents are glycerol, ethylene glycol, and propylene glycol, in a quantity of up to about 30 wt % based on the total agent.

In some embodiments, the addition in particular of glycerol and/or propylene glycol and/or polyethylene glycol and/or polypropylene glycol increases the flexibility of the polymer film formed when the agent is utilized. In embodiments where a flexible hold is desired, the agents preferably contain about 0.01 to about 30 wt % glycerol and/or propylene glycol and/or polyethylene glycol and/or polypropylene glycol, based on the total agent.

In some embodiments, the agents preferably have a pH from about 2 to about 11. In some embodiments, the pH range between about 2 and about 8 is particularly preferred. Unless otherwise noted, indications as to pH refer, for purposes of this document, to the pH at 25° C.

The agents can furthermore contain the adjuvants and additives that are routinely found in conventional styling agents.

The following additional care-providing substances are particular examples of additional adjuvants and additives.

In some embodiments, a silicone oil and/or a silicone gum can be used, for example, as a care-providing substance.

Exemplary silicone oils or silicone gums suitable for inclusion in agents described herein include, in particular, dialkyl- and alkylarylsiloxanes, for example dimethylpolysiloxane and methylphenylpolysiloxane, as well as alkoxylated, quaternized, or also anionic derivatives thereof. Cyclic and linear polydialkylsiloxanes, alkoxylated and/or aminated derivatives thereof, dihydroxypolydimethylsiloxanes, and polyphenylalkylsiloxanes are preferred.

Silicone oils produce a wide variety of effects. For example, they simultaneously influence dry and wet combability, the feel of the dry and wet hair, and shine. The skilled artisan understands the term "silicone oils" as several structures of organosilicon compounds. It is understood firstly as dimethiconols.

The following commercial products are recited as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (all the aforesaid Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all the aforesaid Dow Corning Corporation), Dub Gel S11400 (Stearinerie Dubois Fils), HVM 4852 Emulsion (Crompton Corporation), Jeesilc 6056 (Jeen International Corporation), Lubrasil, Lubrasil DS (both Guardian Laboratories), Nonychosine E, Nonychosine V (both Exsymol), San-Surf Petrolatum-25, Satin Finish (both Collaborative Laboratories, Inc.), Silatex-D30 (Cosmetic Ingredient Resources), Silsoft 148, Silsoft E-50, Silsoft E-623 (all the aforesaid Crompton Corporation), SM555, SM2725, SM2765, SM2785 (all the aforesaid GE Silicones), Taylor T-Sil CD-1, Taylor TME-4050E (all Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforesaid Wacker-Chemie GmbH).

Dimethicones constitute the second group of silicones that can be contained in some embodiments of the agents described herein. They can be both linear and branched, and also cyclic or cyclic and branched.

Dimethicone copolyols (S3) constitute a further group of silicones that are suitable. Corresponding dimethicone copolyols are commercially obtainable and are marketed, for example, by the Dow Corning company under the designation Dow Corning® 5330 Fluid.

It is intended that, in some embodiments, dimethiconols, dimethicones, and/or dimethicone copolymers can already be present as an emulsion. The corresponding emulsion of dimethiconols, dimethicones, and/or dimethicone copolyols can be produced both after manufacture of the corresponding dimethiconols, dimethicones, and/or dimethicone copolyols, from them and using usual emulsification methods known to one skilled in the art. For this purpose both cationic, anionic, nonionic, or zwitterionic surfactants and emulsifier agents can be used, as auxiliaries, as adjuvants for manufacture of the corresponding emulsions. The emulsions of dimethiconols, dimethicones, and/or dimethicone copolyols can of course also be manufactured directly by way of an emulsion polymerization method. Such methods, too, are very familiar to one skilled in the art.

In some embodiments, dimethiconols, dimethicones, and/or dimethicone copolyols are used as an emulsion, and the droplet size of the emulsified particles is equal to about 0.01 to about 10,000 µm, preferably about 0.01 to about 100 µm, particularly preferably about 0.01 to about 20 µm, and very particularly preferably about 0.01 to about 10 µm. The particle size is determined using the light-scattering method.

When branched dimethiconols, dimethicones, and/or dimethicone copolyols are used, this is to be understood to mean that the branching is greater than a random branching that occurs randomly as a result of impurities in the respective monomers. "Branched" dimethiconols, dimethicones, and/or dimethicone copolyols are therefore to be understood to mean that the degree of branching is greater than about 0.01%. A degree of branching greater than about 0.1% is preferred, and very particularly preferably it is greater than about 0.5%. The degree of branching is determined from the ratio of unbranched monomers to the branching monomers, i.e. to the quantity of tri- and tetrafunctional siloxanes. Both low-branching and high-branching dimethiconols, dimethicones, and/or dimethicone copolyols can be very particularly preferred in some embodiments.

Particularly suitable silicones are aminofunctional silicones, in particular the silicones grouped under the INCI name Amodimethicone. It is therefore preferred in some embodiments if the agents additionally contain at least one aminofunctional silicone. These are to be understood as silicones that comprise at least one optionally substituted amino group. These silicones are referred to according to the INCI declaration as Amodimethicone, and are obtainable, for example, in the form of an emulsion as a commercial product Dow Corning® 939, or as a commercial product Dow Corning® 949, mixed with a cationic and a nonionic surfactant.

In some embodiments, those aminofunctional silicones which have an amine number above about 0.25 meq/g, preferably above about 0.3 meq/g, and particularly preferably above about 0.4 meq/g are preferably used. The amine number here denotes the milliequivalent of amine per gram of the aminofunctional silicone; it can be ascertained by titration, and can also be indicated with the "mg KOH/g" unit.

In some embodiments, the agents contain silicones preferably in quantities from about 0.01 wt % to about 15 wt %, particularly preferably from about 0.05 to about 2 wt %, based on the total agent.

In some embodiments, the agent can, for example, contain at least one protein hydrolysate and/or one of its derivatives as a care-providing substance of a different class of compound.

Protein hydrolysates are product mixtures obtained by the acid-, base-, or enzyme-catalyzed breakdown of proteins. As used herein, the term "protein hydrolysates" is also understood to mean total hydrolysates as well as individual amino acids and derivatives thereof, as well as mixtures of different amino acids. In some embodiments, the molecular weight of protein hydrolysates is between about 75 (the molecular weight of glycine) and about 200,000; the molecular weight is preferably equal to about 75 to about 50,000, and very particularly preferably about 75 to 20,000 dalton.

In some embodiments, protein hydrolysates of both vegetable as well as animal or marine or synthetic origin can be used.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm), and Kerasol® (Croda).

In some embodiments, protein hydrolysates are contained in the agents, for example, in concentrations from about 0.01 wt % to about 20 wt %, preferably from about 0.05 wt % to about 15 wt %, and very particularly preferably in quantities from about 0.05 wt % to about 5 wt %, based in each case on the total utilization preparation.

In some embodiments, the agent can further contain at least one vitamin, one provitamin, one vitamin precursor, and/or one derivative thereof as a care-providing substance.

In some embodiments, those vitamins, provitamins, and vitamin precursors which are usually assigned to the groups A, B, C, E, F, and H are preferred.

The group of substances referred to as "vitamin A" includes retinol (vitamin $A_1$) as well as 3,4-didehydroretinol (vitamin $A_2$). β-Carotene is the provitamin of retinol. Vitamin A components include, for example, vitamin A acid and esters thereof, vitamin A aldehyde, and vitamin A alcohol, as well as esters thereof such as the palmitate and acetate. Embodiments comprising a vitamin A component preferably comprise a vitamin A component in a quantity from about 0.05 to about 1 wt %, based on the total utilization preparation.

Members of the vitamin B group or vitamin B complex are, among others, vitamin $B_1$ (thiamine), vitamin $B_2$ (riboflavin), vitamin $B_3$ (nicotinic acid and/or nicotinic acid amide (niacinamide)), vitamin $B_5$ (pantothenic acid, panthenol, and pantolactone), vitamin $B_6$ (pyridoxine as well as pyridoxamine and pyridoxal), vitamin C (ascorbic acid), vitamin E (tocopherols, in particular α-tocopherol), vitamin F (linoleic acid and/or linolenic acid), vitamin H.

In some embodiments, agents preferably contain vitamins, provitamins, and vitamin precursors from the groups A, B, C, E, and H. In some embodiments, panthenol, pantolactone, and pyridoxine and derivatives thereof, as well as nicotinic acid amide and biotin, are particularly preferred.

In some embodiments, d-panthenol is very particularly preferred as a care-providing substance, optionally in combination with at least one of the silicone derivatives recited above.

Like the addition of glycerol and/or propylene glycol, in some embodiments the addition of panthenol increases the flexibility of the polymer film formed upon utilization of the agent. In embodiments where a particularly flexible hold is desired, the agents may thus contain panthenol instead of or in addition to glycerol and/or propylene glycol. In an exemplary embodiment the agents contain panthenol, preferably in a quantity from about 0.05 to about 10 wt %, particularly preferably about 0.1 to about 5 wt %, based in each case on the total agent.

The agents can furthermore contain at least one plant extract as a care-providing substance.

These extracts are usually produced by extraction of the entire plant. In individual cases, however, it may also be preferred to produce the extracts exclusively from blossoms and/or from leaves of the plant.

In some embodiments, the extracts from green tea, oak bark, nettle, witch hazel, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

In some embodiments, it can further be preferred to use in the agents mixtures of several, in particular of two, different plant extracts.

In some embodiments, mono- or oligosaccharides can also be used as a care-providing substance in the agents.

Both monosaccharides and oligosaccharides, for example cane sugar, milk sugar, and raffinose, can be used. In some embodiments, the use of monosaccharides is preferred. In some related embodiments, among the monosaccharides, those compounds which contain 5 or 6 carbon atoms are in turn preferred.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are carbohydrates that are preferably used; it is very particularly preferred to use glucose, which is suitable both in the D-(+) or L-(−) configuration or as a racemate. Derivatives of these pentoses and hexoses, such as the corresponding -onic and -uronic acids (sugar acids), sugar alcohols, and glycosides, can also be used in some embodiments. Preferred sugar acids are gluconic acid, glucuronic acid, saccharic acid, mannosaccharic acid, and mucic acid. Preferred sugar alcohols are sorbitol, mannitol, and dulcitol. Preferred glycosides are methylglucosides.

Because the mono- or oligosaccharides that are used are usually obtained from natural raw materials such as starch, as a rule they exhibit the configurations corresponding to those raw materials (e.g. D-glucose, D-fructose and D-galactose).

Mono- or oligosaccharides are contained in the agents preferably in a quantity from about 0.1 to about 8 wt %, particularly preferably from about 1 to about 5 wt %, based on the total utilization preparation.

In some embodiments, the agent can furthermore contain at least one lipid as a care-providing substance.

In some embodiments, suitable lipids include phospholipids, for example soy lecithin, egg lecithin, and kephalins, as well as the substances known by the INCI names Linoleamidopropyl PG-Dimonium Chloride Phosphate, Cocamidopropyl PG-Dimonium Chloride Phosphate, and Stearamidopropyl PG-Dimonium Chloride Phosphate. These are marketed, for example, by the Mona company under the commercial designations Phospholipid EFA®, Phospholipid PTC®, and Phospholipid SV®. In some embodiments, the agents contain lipids preferably in quantities from about 0.01 to about 10 wt %, in particular about 0.1 to about 5 wt %, based on the total utilization preparation.

Oily substances are furthermore suitable as a care-providing substance.

Included among the natural and synthetic cosmetic oils are, for example:

Vegetable oils. Examples of such oils are sunflower oil, olive oil, soy oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditert-butyl ether, diisopentyl ether, di-3-ethyldecyl ether, tert-butyl-n-octyl ether, isopentyl-n-octyl ether, and 2-methylpentyl-n-octyl ether. In some embodiments, the compounds 1,3-di-(2-ethylhexyl)cyclohexane (Cetiol® S) and di-n-octyl ether (Cetiol® OE), available as commercial products, can be preferred.

Ester oils. "Ester oils" are to be understood as esters of $C_6$ to $C_{30}$ fatty acids with $C_2$ to $C_{30}$ fatty alcohols. In some embodiments, nonoesters of fatty acids with alcohols having 2 to 24 carbon atoms are preferred. In some particular embodiments, isopropyl myristate (Rilanit® IPM), isononanoic acid C16-18 alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

dicarboxylic acid esters such as di-n-butyl adipate, di-(2-ethylhexyl) adipate, di-(2-ethylhexyl) succinate, and diisotridecyl acelaate, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate, symmetrical, asymmetrical, or cyclic esters of carbonic acid with fatty alcohols, described e.g. in German Application 197 56 454, glycerol carbonate or dicaprylyl carbonate (Cetiol® CC), fatty acid triesters of saturated and/or unsaturated linear and/or branched fatty acids with glycerol, fatty acid partial glycerides, i.e. monoglycerides, diglycerides, and industrial mixtures thereof. When industrial products are used, small quantities of triglycerides may still be present for manufacturing-related reasons. The partial glycerides preferably conform to formula (D4-I),

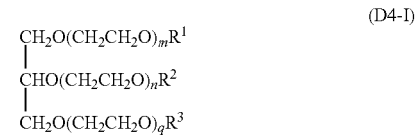

(D4-I)

in which $R^1$, $R^2$ and $R^3$ mutually independently denote hydrogen or a linear or branched, saturated and/or unsaturated acyl residue having 6 to 22, preferably 12 to 18 carbon atoms, with the provision that at least one of these groups denotes an acyl residue and at least one of these groups denotes hydrogen. The sum (m+n+q) denotes 0 or numbers from 1 to 100, preferably 0 or 5 to 25. Preferably $R^1$ denotes an acyl residue and $R^2$ and $R^3$ denote hydrogen, and the sum (m+n+q) is 0. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as industrial mixtures thereof. Oleic acid monoglycerides are preferably used.

In some embodiments, the quantity of natural and synthetic cosmetic oily substances used in the agents is usually about 0.1 to about 30 wt %, based on the total utilization preparation, preferably about 0.1 to about 20 wt %, and in particular about 0.1 to about 15 wt %.

Although each of the aforesaid care-providing substances by itself already provides a satisfactory result, embodiments in which the agent contains multiple care-providing substances, including from different groups, are also included.

The addition of a UV filter allows both the agents themselves, and the treated fibers, to be protected from damaging influences of UV radiation. At least one UV filter is therefore preferably added to the agent in some embodiments. The suitable UV filters are not subject to any general restrictions in terms of their structure and their physical properties. Instead, all UV filters usable in the cosmetics sector, whose absorption maximum lies in the UVA (315 to 400 nm) UVB (280 to 315 nm), or UVC (<280 nm) regions, are suitable. UV filters having an absorption maximum in the UVB region, in particular in the region from approximately 280 to approximately 300 nm, are particularly preferred.

In some embodiments, the UV filters can be selected, for example, from substituted benzophenones, p-aminobenzoic acid esters, diphenylacrylic acid esters, cinnamic acid esters, salicylic acid esters, benzimidazoles, and o-aminobenzoic acid esters.

Examples of UV filters include 4-aminobenzoic acid, N,N,N-trimethyl-4-(2-oxoborn-3-ylidenemethyl)aniline methylsulfate, 3,3,5-trimethylcyclohexyl salicylate (Homosalate), 2-hydroxy-4-methoxybenzophenone, 2-phenylbenzimidazole-5-sulfonic acid and potassium, sodium, and triethanolamine salts thereof, 3,3'-(1,4-phenylenedimethylene)-bis(7,7-dimethyl-2-oxobicyclo-[2.2.1]hept-1-yl-methanesulfonic acid) and salts thereof, 1-(4-tert-butylphenyl)-3-(4-methoxyphenyl)propane-1,3-dione, α-(2-oxoborn-3-ylidene)toluene-4-sulfonic acid and salts thereof, ethoxylated 4-aminobenzoic acid ethyl ester (PEG-25 PABA; Uvinul®P 25), 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and the sodium salt thereof (Benzophenone-4; Uvinul® MS 40; Uvasorb® S 5), 3-(4'-methylbenzylidene) D,L-camphor, 3-benzylidene camphor (3-Benzylidene Camphor), 4-isopropylbenzyl salicylate, 2,4,6-trianilino-(p-carbo-2'-ethylhexyl-1'-oxy)-1,3,5-triazine, 3-imidazol-4-ylacrylic acid and ethyl esters thereof, polymers of N-{(2 and 4)[2-oxoborn-3-ylidenemethyl]benzyl}acrylamide, 2,4-dihydroxybenzophenone, 1,1'-diphenylacrylonitrilic acid 2-ethylhexyl ester, o-aminobenzoic acid menthyl ester, 2,2',4,4'-tetrahydroxybenzophenone, 2,2'-dihydroxy-4,4'-dimethoxybenzophenone, 2,2'-dihydroxy-4,4'-dimethoxybenzophenone-5-sodiumsulfonate, and 2-cyano-3,3-diphenylacrylic acid 2'-ethylhexyl ester. In some embodiments, 2-hydroxy-4-methoxy-benzophenone-5-sulfonic acid and the sodium salt thereof, and/or ethoxylated 4-aminobenzoic acid ethyl ester, are preferred.

UV filters are contained usually in quantities from about 0.01 to about 5 wt %, based on the total utilization preparation. Quantities from about 0.1 to about 2.5 wt % are preferred.

In a particular embodiment, the agent furthermore contains one or more substantive dyes. This allows the keratinic fibers treated upon use of the agent to be not only temporarily structured, but at the same time also dyed. This can be desirable in particular when what is desired is only a temporary coloration, for example with conspicuous "fashion" colors, which can be removed again from the keratinic fibers simply by washing.

Substantive dyes are usually nitrophenylenediamines, nitroaminophenols, azo dyes, anthraquinones, or indophenols. In some embodiments, preferred substantive dyes are the compounds known by the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-1-hydroxy-4-nitrobenzene. In some embodiments, it is preferred to use cationic substantive dyes. Particularly preferred in this context are (a) cationic triphenylmethane dyes such as, for example, Basic Blue 7, Basic Blue 26, Basic Violet 2, and Basic Violet 14;

(b) aromatic systems that are substituted with a quaternary nitrogen group, for example Basic Yellow 57, Basic Red 76, Basic Blue 99, Basic Brown 16, and Basic Brown 17; and (c) substantive dyes that contain a heterocycle which comprises at least one quaternary nitrogen atom, such as those recited, for example, in Claims 6 to 11 of EP-A2-998 908, to which reference is explicitly made at this juncture.

In some embodiments, the dyes also known by the designations Basic Yellow 87, Basic Orange 31, and Basic Red 51 are very particularly preferred cationic substantive dyes of group (c). In some particular embodiments, the cationic substantive dyes that are marketed under the trademark Arianor® are likewise cationic substantive dyes very particularly preferred.

In some embodiments, the agents contain substantive dyes preferably in a quantity from about 0.001 to about 20 wt %, based on the total agent.

In some embodiments, it is preferred that the agents be free of oxidation dye precursors. Oxidation dye precursors are divided into so-called developer components and coupler components. The developer components form the actual dyes with one another under the influence of oxidizing agents or atmospheric oxygen, or by coupling with one or more coupler components.

The agents can be formulated in any form usual for styling agents, for example in the form of solutions that can be applied onto the hair as a hair lotion or as a pump or aerosol spray, in the form of creams, emulsions, waxes, gels, or also surfactant-containing foaming solutions or other preparations that are suitable for application to the hair.

Hair creams and hair gels generally contain structuring agents and/or thickening polymers which serve to impart the desired consistency to the products. Structuring agents and/or thickening polymers are used typically in a quantity from about 0.1 to about 10 wt %, based on the total product. In some embodiments, quantities from about 0.5 to about 5 wt %, in particular about 0.5 to about 3 wt %, are preferred.

The agents are preferably packaged as a pump spray, aerosol spray, pump foam, or aerosol foam.

For this, the agents are packaged in a delivery apparatus that represents either a pressurized-gas container additionally filled with a propellant ("aerosol container") or a non-aerosol container.

The pressurized-gas containers with which a product is distributed through a valve as a result of the internal gas pressure of the container are referred to by definition as "aerosol containers." A "non-aerosol container" is defined, conversely to the "aerosol" definition, as a vessel under standard pressure with which a product is distributed by means of mechanical action by way of a pump system.

In some particular embodiments, the agents are packaged particularly preferably as an aerosol hair foam or aerosol hair spray. The agent (in particular the preferred embodiments (A) to (F)) (see above) therefore preferably additionally contains at least one propellant.

Suitable propellants are selected, for example, from $N_2O$, dimethyl ether, $CO_2$, air, alkanes having 3 to 5 carbon atoms such as propane, n-butane, isobutane, n-pentane, and isopentane, and mixtures thereof. In some embodiments, dimethyl ether, propane, n-butane, isobutane, and mixtures thereof are preferred.

According to a preferred embodiment, the aforesaid alkanes, mixtures of the aforesaid alkanes, or mixtures of the aforesaid alkanes with dimethyl ether are used as the only propellant. Concurrent use of propellants of the chlorofluorocarbon type, but in particular fluorocarbons, is also expressly encompassed.

For a given spray apparatus, the sizes of the respective aerosol droplets or foam bubbles, and the respective size distribution, can be adjusted by way of the quantitative ratio between the propellant and the other constituents of the preparations.

The quantity of propellant used varies as a function of the specific composition of the agent, the packaging used, and the desired type of product (e.g. hair spray or hair foam). When conventional spray apparatuses are used, aerosol foam products contain the propellant preferably in quantities from about 1 to about 35 wt %, based on the total product. Quantities from about 2 to about 30 wt %, in particular from about 3 to about 15 wt %, are particularly preferred. Aerosol sprays generally contain larger quantities of propellant. In this case the propellant is used preferably in a quantity from about 30 to about 98 wt %, based on the total product. Quantities from about 40 to about 95 wt %, in particular from about 50 to about 95 wt %, are particularly preferred.

The aerosol products can be manufactured in usual fashion. As a rule all the constituents of the particular agent, with the exception of the propellant, are introduced into a suitable pressure-tight container. The latter is then sealed with a valve. Lastly, the desired quantity of propellant is introduced using conventional techniques.

Isopentane is preferably suitable as a propellant for foaming gel-type agents in a two-chamber aerosol container, which propellant is incorporated into an agent and is packaged in the first chamber of the two-chamber aerosol container. Packaged in the second chamber of the two-chamber aerosol container is at least one further propellant, different from isopentane, that builds up in the two-chamber aerosol container a higher pressure than the isopentane. In some embodiments, the propellants of the second chamber are preferably selected from $N_2O$, dimethyl ether, $CO_2$, air, alkanes having 3 or 4 carbon atoms (such as propane, n-butane, isobutane), and mixtures thereof.

A preferred embodiment is an aerosol hair foam or aerosol hair spray containing an agent described above, and at least one propellant.

Preferred agents and propellants formulated as an aerosol hair foam or aerosol hair spray, as well as the respective quantities of propellant, correspond to the statements already made above.

Another aspect provided herein is the use of the agents described herein for the temporary deformation of hair and/or for hair care.

The agents described herein, and products that contain these agents, in particular aerosol hair foams or aerosol hair sprays, are notable in particular for the fact that they impart a very strong, durable hairstyle hold to the treated hair, even though the hair remains flexible. If the agent is packaged as a hair foam, a stable, fine-pored, and creamy foam forms, which can be distributed onto the hair evenly and without dripping.

Another aspect provided herein is a method for treating keratin-containing fibers, in particular human hair, in which, using a delivery apparatus, an agent is foamed into a foam and the resulting foam is applied onto the keratin-containing fibers.

In some embodiments, it is preferred that a shape be imparted to the keratin-containing fibers, and that that shape be fixed in place by an agent described herein.

The delivery apparatuses recited earlier (see above) are considered preferred.

Another aspect provided herein is a method for treating keratin-containing fibers, in particular human hair, in which, using a delivery apparatus, an agent described herein is applied as a spray onto the keratin-containing fibers.

In some embodiments, it is preferred that a shape be imparted to the keratin-containing fibers, and that that shape be fixed in place by an agent described herein.

The delivery apparatuses recited earlier (see above) are considered preferred.

EXAMPLES

Unless otherwise noted, the following quantity indications are understood to be percentages by weight.

The following formulas were prepared by mixing the raw materials indicated:

| Raw materials | E1 | V1 | V2 |
| --- | --- | --- | --- |
| 2-Amino-2-methylpropan-1-ol | 0.067 | — | 0.134 |
| Aquastyle ® 300[1] | 2.50 | 5.00 | — |
| Gantrez ES 425[2] | 1.50 | — | 3.00 |
| Water | | to 100 | |

[1]INCI name: Polyquaternium-69 (30 wt % active substance in ethanol/water mixture, molecular weight 350,000) (Ashland),
[2]Copolymer of methyl vinyl ether and the butyl semi-ester of maleic acid (50 wt % active substance in ethanol), INCI name: Butyl Ester of PVM/MA Copolymer (Ashland)

Standardized hair strands of the Kerling company (item no. 827560), hair type "European Natural," color 6/0, with a length ($L_{max}$) of 220 mm and a weight of 0.6 g, were used.

For preparation, the strands were washed with 12.5-wt % sodium laureth sulfate solution. The hair strands were dried overnight in a drying oven at 318 K.

0.18 g of the compositions was respectively applied onto each hair strand and massaged in. The strands were then wound onto a curler (Fripac-medis, diam. 7 mm, item no. D-1203) and dried overnight at room temperature.

The curlers were then carefully removed, and the strands were suspended. The length of each of the curls was measured ($L_0$), and the strands were put into a climate chamber. They were stored there at 294 K and a relative humidity of 85% for a period of 24 h, and the lengths of the curls were then measured again ($L_t$).

Five test strands were correspondingly treated and measured for each composition.

High humidity curl retention (HHCR) was calculated using the formula below, and the arithmetic mean of HHCR values for the five test strands was obtained for each composition:

$$HHCR = \frac{L_{max} - L_t}{L_{max} - L_0}$$

HHCR E1: 97%
HHCR V1: 82%
HHCR V2: 29%

The polymer combination of agent E1 (total of 1.5 wt % polymer active substance) exhibits a significantly higher HHCR than the same quantity of polymer (1.5 wt % active substance) of the respective individual polymer of the comparison compositions V1 and V2.

The invention claimed is:

1. A cosmetic agent for cosmetic treatment of keratin-containing fibers comprising:
    (a) about 0.1 wt. % to about 5.0 wt. %, relative to the weight of the agent, of at least one amphiphilic cationic polymer comprising at least one structural unit of formula (I), at least one structural unit of formula (II), at least one structural unit of formula (III), and at least one structural unit of formula (IV),

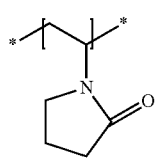
(I)

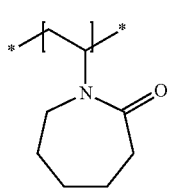
(II)

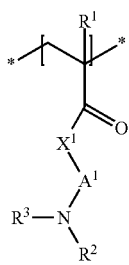
(III)

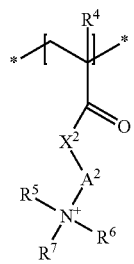
(IV)

in which
    $R^1$ and $R^4$ mutually independently denote a hydrogen atom or a methyl group,
    $X^1$ and $X^2$ mutually independently denote an oxygen atom or an NH group,
    $A^1$ and $A^2$ mutually independently denote an ethane-1,2-diyl group, propane-1,3-diyl group, or butane-1,4-diyl group,
    $R^2$, $R^3$, $R^5$, and $R^6$ mutually independently denote a ($C_1$ to $C_4$) alkyl group,
    $R^7$ denotes a ($C_8$ to $C_{30}$) alkyl group,
    (b) about 0.1 wt. % to about 5.0 wt. %, relative to the weight of the agent, of at least one copolymer comprising at least one structural unit of formula (A1) and at least one structural unit of formula (A2),

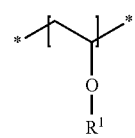
(A1)

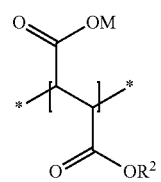
(A2)

in which
    $R^1$ denotes a ($C_1$ to $C_{18}$) alkyl group,
    $R^2$ denotes a ($C_1$ to $C_6$) alkyl group,
    M denotes a hydrogen atom or an equivalent of a mono- or polyvalent cation, and
    (c) a cosmetically acceptable carrier
        wherein the ratio (W/W) of the at least one copolymer (a) to the at least one copolymer (b) is about 5:1 to 1:5.

2. The cosmetic agent according to claim 1, wherein $R^1$ and $R^4$ in formula (III) or formula (IV) each signify a methyl group.

3. The cosmetic agent according to claim 1 wherein $A^1$ and $A^2$ in formula (III) or formula (IV) mutually independently denote ethane-1,2-diyl or propane-1,3-diyl.

4. The cosmetic agent according to claim 1, wherein $R^2$, $R^3$, $R^5$, and $R^6$ in formula (III) or formula (IV) mutually independently denote methyl or ethyl.

5. The cosmetic agent according to claim 1, wherein $R^7$ in formula (IV) denotes a $C_{10}$ to $C_{24}$ alkyl group.

6. The cosmetic agent according to claim 1, wherein the amphiphilic cationic polymer comprises at least one structural unit of formula (II), at least one structural unit of formula (III-8), and at least one structural unit of formula (IV-8)

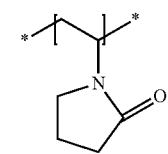
(I)

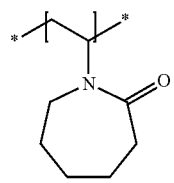
(II)

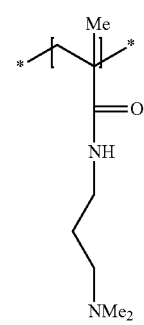
(III-8)

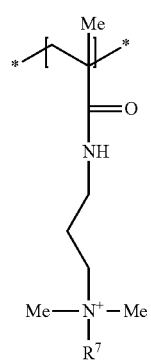
(IV-8)

in which R⁷ denotes octyl (capryl), decyl (caprinyl), dodecyl (lauryl), tetradecyl (myristyl), hexadecyl (cetyl), octadecyl (stearyl), eicosyl (arachyl), or docosyl (behenyl).

7. The cosmetic agent according to claim 1, wherein $R^1$ in formula (A1) denotes a methyl group.

8. The cosmetic agent according to claim 1, wherein $R^2$ in accordance with formula (A2) denotes a ($C_2$ to $C_4$) alkyl group.

9. The cosmetic agent according to claim 1, further comprising at least one alkanolamine.

10. The agent according to claim 1, wherein the keratin-containing fibers are human hair.

11. The agent according to claim 4, wherein $R^2$, $R^3$, $R^5$, and $R^6$ in formula (III) or formula (IV) mutually independently denote methyl.

12. The agent according to claim 5, wherein $R^7$ in formula (IV) denotes decyl (caprinyl), dodecyl (lauryl), tetradecyl (myristyl), hexadecyl (cetyl), octadecyl (stearyl), eicosyl (arachyl), or docosyl (behenyl).

13. The cosmetic agent according to claim 8, wherein $R^2$ in accordance with formula (A2) denotes an ethyl, n-propyl, isopropyl, n-butyl, or tert-butyl group.

14. A method for treating keratin-containing fibers, the method comprising:
applying a cosmetic agent to keratin-containing fibers, the cosmetic agent comprising:
(a) about 0.1 wt. % to about 5.0 wt. %, relative to the weight of the agent, of at least one amphiphilic cationic polymer comprising at least one structural unit of formula (I), at least one structural unit of formula (II), at least one structural unit of formula (III), and at least one structural unit of formula (IV),

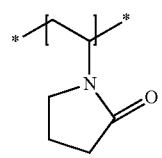
(I)

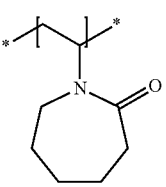
(II)

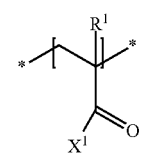
(III)

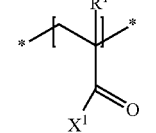
(IV)

in which
$R^1$ and $R^4$ mutually independently denote a hydrogen atom or a methyl group,
$X^1$ and $X^2$ mutually independently denote an oxygen atom or an NH group,
$A^1$ and $A^2$ mutually independently denote an ethane-1,2-diyl group, propane-1,3-diyl group, or butane-1,4-diyl group,
$R^2$, $R^3$, $R^5$, and $R^6$ mutually independently denote a ($C_1$ to $C_4$) alkyl group,
$R^7$ denotes a ($C_8$ to $C_{30}$) alkyl group,
(b) about 0.1 wt. % to about 5.0 wt. %, relative to the weight of the agent, of at least one copolymer comprising at least one structural unit of formula (A1) and at least one structural unit of formula (A2),

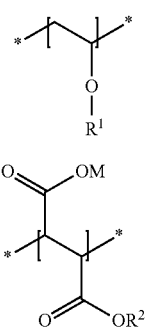

in which
R¹ denotes a ($C_1$ to $C_{18}$) alkyl group,
R² denotes a ($C_1$ to $C_6$) alkyl group,
M denotes a hydrogen atom or an equivalent of a mono- or polyvalent cation, and (c) a cosmetically acceptable carrier
wherein the ratio (W/W) of the at least one copolymer (a) to the at least one copolymer (b) is about 5:1 to 1:5.

15. The method according to claim 14, wherein the keratin-containing fibers are hair, and application of the cosmetic is for temporary deformation of hair and/or hair care.

16. The method according to claim 14, wherein the keratin-containing fibers are human hair.

17. The method according to claim 14, wherein the cosmetic agent is a foam.

18. The method according to claim 14, wherein the cosmetic agent is a liquid and applying the cosmetic agent comprises spraying the liquid cosmetic agent onto the keratin-containing fibers.

19. The agent according to claim 1, wherein the ratio (W/W) of the at least one copolymer (a) to the at least one copolymer (b) is about 2:1 to 1:2.

* * * * *